(12) United States Patent
Mullis

(10) Patent No.: US 8,263,082 B2
(45) Date of Patent: Sep. 11, 2012

(54) CHEMICALLY PROGRAMMABLE IMMUNITY

(75) Inventor: Kary Mullis, Corona del Mar, CA (US)

(73) Assignee: Altermune Technologies LLC, Corona Del Mar, CA (US)

( * ) Notice: Subject to any disclaimer, the term of this patent is extended or adjusted under 35 U.S.C. 154(b) by 0 days.

(21) Appl. No.: 12/685,257

(22) Filed: Jan. 11, 2010

(65) Prior Publication Data

US 2010/0247535 A1  Sep. 30, 2010

Related U.S. Application Data

(63) Continuation of application No. 10/754,456, filed on Jan. 9, 2004, now Pat. No. 7,645,743, which is a continuation-in-part of application No. 10/696,770, filed on Oct. 29, 2003, now Pat. No. 7,422,746, which is a continuation-in-part of application No. 10/178,046, filed on Jun. 21, 2002, now abandoned, which is a continuation of application No. PCT/US00/35179, filed on Dec. 21, 2000.

(60) Provisional application No. 60/171,707, filed on Dec. 22, 1999.

(51) Int. Cl.
| A61K 39/00 | (2006.01) |
| A61K 39/395 | (2006.01) |
| A61K 31/7088 | (2006.01) |

(52) U.S. Cl. ................ 424/178.1; 424/193.1; 514/44 R

(58) Field of Classification Search .................. None
See application file for complete search history.

(56) References Cited

U.S. PATENT DOCUMENTS

| 4,169,137 A | 9/1979 | Hirschfeld et al. |
| 4,243,749 A | 1/1981 | Sadeh et al. |
| 4,711,955 A | 12/1987 | Ward et al. |
| 4,737,453 A | 4/1988 | Primus |
| 4,940,670 A | 7/1990 | Rhodes |
| 5,017,558 A | 5/1991 | Vyas |
| 5,204,449 A | 4/1993 | Puri |
| 5,218,088 A | 6/1993 | Gorenstein et al. |
| 5,378,815 A | 1/1995 | Krsmanovic et al. |
| 5,475,096 A | 12/1995 | Gold et al. |
| 5,637,459 A | 6/1997 | Burke et al. |
| 5,683,867 A | 11/1997 | Biesecker et al. |
| 5,869,232 A | 2/1999 | Sallberg |
| 6,040,137 A | 3/2000 | Sallberg |
| 6,054,312 A | 4/2000 | Larocca et al. |
| 6,090,381 A | 7/2000 | Leung et al. |

(Continued)

FOREIGN PATENT DOCUMENTS

AU  2005213962  2/2010

(Continued)

OTHER PUBLICATIONS

Written Opinion for PCT/US2005/000490, Dec. 4, 2006.*

(Continued)

*Primary Examiner* — David A Saunders
(74) *Attorney, Agent, or Firm* — Davis Wright Tremaine LLP

(57) ABSTRACT

Methods and compositions for immediately immunizing an individual against any molecule or compound. The present invention comprises an immunity linker with at least two sites; (1) at least one first binding site that binds to an immune response component in an individual that has been pre-immunized with a universal immunogen, and (2) at least one second binding site that binds specifically to a desired compound or molecule, the target.

16 Claims, No Drawings

U.S. PATENT DOCUMENTS

| | | | |
|---|---|---|---|
| 6,232,071 | B1 | 5/2001 | Hicke et al. |
| 6,245,895 | B1 | 6/2001 | Sallberg |
| 6,248,332 | B1 | 6/2001 | Romet-Lemonne et al. |
| 6,261,774 | B1 | 7/2001 | Pagratis et al. |
| 6,261,783 | B1 | 7/2001 | Jayasena et al. |
| 6,280,932 | B1 | 8/2001 | Parma et al. |
| 6,280,943 | B1 | 8/2001 | Drolet et al. |
| 6,300,074 | B1 | 10/2001 | Gold et al. |
| 6,329,145 | B1 | 12/2001 | Janjic et al. |
| 6,331,394 | B1 | 12/2001 | Ruckman et al. |
| 6,331,398 | B1 | 12/2001 | Gold et al. |
| 6,344,318 | B1 | 2/2002 | Gold et al. |
| 6,344,321 | B1 | 2/2002 | Rabin et al. |
| 6,346,611 | B1 | 2/2002 | Pagratis et al. |
| 6,376,474 | B1 | 4/2002 | Heilig et al. |
| 6,387,620 | B1 | 5/2002 | Smith et al. |
| 6,387,635 | B1 | 5/2002 | Drolet et al. |
| 6,395,888 | B1 | 5/2002 | Biesecker et al. |
| 6,660,842 | B1 | 12/2003 | Sallberg |
| 6,867,289 | B1 | 3/2005 | Gorenstein et al. |
| 6,933,366 | B2 | 8/2005 | Sallberg et al. |
| 7,033,594 | B2 | 4/2006 | Low et al. |
| 7,112,328 | B2 | 9/2006 | Marinkovich |
| 7,422,746 | B2 | 9/2008 | Mullis |
| 7,645,743 | B2 | 1/2010 | Mullis |
| 7,850,975 | B2 * | 12/2010 | Mullis .................... 424/193.1 |
| 2001/0031252 | A1* | 10/2001 | Low et al. ................ 424/85.2 |
| 2003/0017134 | A1* | 1/2003 | Reiter et al. .............. 424/85.1 |
| 2003/0017165 | A1 | 1/2003 | Mullis |
| 2003/0108555 | A1* | 6/2003 | Marinkovich ............ 424/178.1 |
| 2004/0253679 | A1 | 12/2004 | Epstein et al. |
| 2005/0019333 | A1* | 1/2005 | Sallberg .................... 424/160.1 |
| 2006/0002891 | A1 | 1/2006 | Pouletty |
| 2007/0148183 | A1 | 6/2007 | Mullis |
| 2009/0142368 | A1 | 6/2009 | Mullis |

FOREIGN PATENT DOCUMENTS

| | | |
|---|---|---|
| EP | 0 429 816 A1 | 10/1990 |
| EP | 1 242 115 B1 | 6/2009 |
| WO | WO 92/08491 A1 | 5/1992 |
| WO | WO 95/05454 | 2/1995 |
| WO | WO 95/29938 A1 | 11/1995 |
| WO | WO 97/37690 A2 | 10/1997 |
| WO | WO 01/25416 A1 | 4/2001 |
| WO | WO 01/32207 A1 | 5/2001 |
| WO | WO 01/45734 A1 | 6/2001 |
| WO | WO 2005/079423 A2 | 9/2005 |

OTHER PUBLICATIONS

International Search Report for WO 2005/079423, pp. 1, Nov. 30, 2005.
International Search Report for WO 2001/45734, pp. 1-6, Jun. 5, 2001.
Office Action for U.S. Appl. No. 10/754,456, pp. 1-8, Apr. 1, 2008.
Office Action for U.S. Appl. No. 11/606,564, pp. 1-11, Sep. 22, 2008.
Office Action for U.S. Appl. No. 10/754,456, pp. 1-7, Jun. 22, 2009.
Office Action for U.S. Appl. No. 11/606,564, pp. 1-14, Jan. 29, 2009.
Office Action for U.S. Appl. No. 11/606,564, pp. 1-8, Mar. 21, 2008.
Office Action for U.S. Appl. No. 11/606,564, pp. 1-6, Feb. 23, 2010.
Office Action for U.S. Appl. No. 10/754,456, pp. 1-18, Jun. 1, 2007.
Office Action for U.S. Appl. No. 10/754,456, pp. 1-9, Dec. 12, 2008.
Office Action for U.S. Appl. No. 11/606,564, pp. 1-13, Jul. 22, 2009.
Office Action for U.S. Appl. No. 12/336,746, pp. 1-7, Jun. 16, 2010.
Ahnert-Hilger et al., Monoclonal Antibodies Against Tetanus Toxin and Toxoid, *Medical Microbiology and Immunology*, vol. 172 (2), pp. 123-135, Jul. 1, 1983.
Alexander et al., Altering the Antigenicity of Proteins, *Proceedings of the National Academy of Sciences of the United States of America*, vol. 89 (8), pp. 3352-3356, Apr. 15, 1992.
Brem et al., *J. Neurosurg.*, vol. 74, pp. 441-446, Jan. 1, 1991.
Brown et al., Redirecting the Immune System: An Interview with Dr. Kary Mullis, *Smart Publications*, Mar. 15, 2007.
Bruno et al., In Vitro Selection of DNA Aptamers to Anthrax Spores with Electrochemilurninescence Detection, *Biosensors& Bioelectronics*, vol. 14 (5), pp. 457-464, Apr. 1, 1999.
Carlson, Aptamers: The New Frontier in Drug Development?, *Biotechnology Healthcare*, pp. 31-36, Apr. 1, 2007.
Carter, JM, Epitope Mapping of a Protein Using the Geysen (PEPSCAN) Procedure, *Methods in Molecular Biology*, vol. 36, pp. 207-223, Jan. 1, 1994.
Colas et al., Genetic Selection of Peptide Aptamers that Recognize and Inhibit Cyclin-Dependent Kinase 2, *Nature*, vol. 380 (6574), pp. 548-550, Apr. 11, 1996.
Conrad et al., In Vitro Selection of Nucleic Acid Aptamers that Bind Proteins, *Methods in Enzymology*, vol. 267, pp. 336-367, Jan. 1, 1996.
Edmundson et al., Principles and Pitfalls in Designing Site-Directed Peptide Ligands, *Proteins*, vol. 16 (3), pp. 246-267, Jul. 1, 1993.
Edmundson et al., Binding of Peptides to Proteins: An Exercise in Molecular Design, *Ciba Foundation Symposium*, vol. 158, pp. 213-230, Jan. 1, 1991.
Famulok et al., Aptamers as Tools in Molecular Biology and Immunology, *Current Topics in Microbiology and Immunology*, vol. 243, pp. 123-135, Jan. 1, 1999.
Finberg et al., The Use of Antiidiotypic Antibodies as Vaccines Against Infectious Agents, *CRC Critical Reviews in Immunology*, vol. 7 (4), pp. 269-284, Jan. 1, 1987.
Fitzwater et al., A SELEX Primer, *Methods in Enzymology*, vol. 267, pp. 275-301, Jan. 1, 1996.
Galili et al., Chapter I: Evolution of 1,3Galactosyltransferase and of the -Gal Epitope, *Subcellular Biochemistry*, vol. 32, pp. 1-23, Jan. 1, 1999.
Geysen et al., Use of Peptide Synthesis to Probe Viral Antigens for Epitopes to a Resolution of a Single Amino Acid, *Proceedings of the National Academy of Sciences of the United States of America*, vol. 81 (13), pp. 3998-4002, Jul. 1, 1984.
Geysen et al., Strategies for Epitope Analysis using Peptide Synthesis, *Journal of Immunological Methods*, vol. 102, pp. 259-274, Sep. 24, 1987.
Geysen et al., Isotope or Mass Encoding of Combinatorial Libraries, *Chemistry & Biology*, vol. 3 (8), pp. 679-688, Aug. 1, 1996.
Glennie et al., Preparation and Performance of Bispecific F(ab'γ)$_2$ Antibody Containing Thioether-Linked Fab'γ Fragments, *The Journal of Immunology*, vol. 139 (7), pp. 2367-2375, Oct. 1, 1987.
Herbert et al., Dictionary of Immunology, vol. 3rd Ed., pp. 3-4, Jan. 1, 1985.
Janczuk et al., a-Gal Oligosaccharides: Chemistry and Potential Biomedical Application, *Current Medicinal Chemistry*, vol. 6 (2), pp. 155-164, Jan. 1, 1999.
Jayasena, S. D. Aptamers: An Emerging Class of Molecules that Rival Antibodies in Diagnostics, *Clinical Chemistry*, vol. 45 (9), pp. 1628-1650, Jan. 1, 1999.
Nielsen et al., Synthesis and Character of Dinucleoside Phosphorodithioates, *Tetrahedron Lett.* vol. 29 (24), pp. 2911-2914, Jan. 1, 1988.
Ringquist et al., Anti-L-Selectin Oligonucleotide Ligands Recognize CD62L-Positive Leukocytes: Binding Affinity and Specificity of Univalent and Bivalent Ligands, *Cytometry*, vol. 33 (4), pp. 394-405, Dec. 1, 1998.
Rodda et al., Multipin Technology in the Preparation and Screening of Peptide Libraries, *Australasian Biotechnology*, vol. 3 (6), pp. 346-247, Nov. 1, 1993.
Schultz, JS The Combinatorial Library: A Multifunctional Resource, *Biotechnology Progress*, vol. 12 (6), pp. 729-743, Nov. 1, 1996.
Smith, GP Surface Presentation of Protein Epitopes using Bacteriophage Expression Systems, *Current Opinions in Biotechnology*, vol. 2 (5), pp. 668-673, Oct. 1, 1991.
Tribbick et al., Systematic Fractionation of Serum Antibodies using Multiple Antigen Homologous Peptides as Affinity Ligands, *Journal of Immunological Methods*, vol. 139 (2), pp. 155-156, Jun. 3, 1991.
Valerio et al., Multipin Peptide Synthesis at the Micromole Scale using 2-Hydroxyethyl Methacrylate Grafted Polyethylene Supports, *International Journal of Peptide and Protein Synthesis*, vol. 42(1), pp. 1-9, Jul. 1, 1993.
Vater et al., Toward Third-Generation Aptamers: Spiegelmers and Their Therapeutic Prospects, *Current Opin. Drug Discov. Devel.* vol. 6(2), 253-261, Mar. 1, 2003.

Wagner et al., Ratio Encoding Combinatorial Libraries with Stable Isotopes and Their Utility in Pharmaceutical Research, *Combinatorial Chemistry and High Throughput Screening*, vol. 1 (3), pp. 143-153, Oct. 1, 1998.

Weiner et al., Bispecific Anti-Idiotype/Anti-CD3 Antibody Therapy of Murine B Cell Lymphoma, *The Journal of Immunology*, vol. 147 (11), pp. 4035-4044, Dec. 1, 1991.

Xu et al., Anti-peptide Aptamers Recognize Amino Acid Sequence and Bind a Protein Epitope, *Proceedings of the National Academy of Sciences of the United States of America*, vol. 93 (15), pp. 7475-7480, Jul. 23, 1996.

International Search Report and Written Opinion for International Application No. PCT/US2010/33716, pp. 1-6, Aug. 6, 2010.

EPO Office Action—Appl. No. 00990960.7, *EPO Office Action*, pp. 1-7, Oct. 17, 2005.

EPO Supplementary Search Report—Appl. No. 00990960.7, *EPO Search*, pp. 1-6, Apr. 29, 2004.

EPO Office Action—Appl. No. 00990960.7, *EPO Office Action*, pp. 1-4, Apr. 2, 2007.

EPO Supplementary Search Report—Appl. No. 05751992.8, *EPO Search Report*, pp. 1-4, Oct. 6, 2008.

EPO Office Action—Appl. No. 05751992.8, *EPO Office Action*, pp. 1-7, Dec. 3, 2008.

AU Office Action—Appl. No. 2005213962, *Australian Patent Office*, pp. 1-2, Aug. 19, 2006.

AU Office Action—Appl. No. 2005213962, *Australian Patent Office*, pp. 1-4, May 5, 2009.

Davis et al., Use of a High affinity DNA Ligand in Flow Cytometry, *Nucleic Acids Research*, vol. 24 (4), pp. 702-706, Jan. 1, 1996.

Office Action for U.S. Appl. No. 11/606,564, *U.S. PTO Office Action*, pp. 1-14, Jan. 29, 2009.

Office Action for U.S. Appl. No. 12/336,746, *U.S. PTO Office Action*, pp. 1-7, Jun. 16, 2010.

Office Action for U.S. Appl. No. 10/178,046, *U.S. PTO Office Action*, pp. 1-6, Jan. 11, 2006.

Office Action for U.S. Appl. No. 10/696,770, *U.S. PTO Office Action*, pp. 1-13, Sep. 12, 2006.

Office Action for U.S. Appl. No. 10/696,770, *U.S. PTO Office Action*, pp. 1-16, Jan. 17, 2008.

Office Action for U.S. Appl. No. 10/754,456, *U.S. PTO Office Action*, pp. 1-14, Sep. 8, 2006.

White et al., Developing Aptamers into Therapeutics, *The Journal of Clinical Investigation*, vol. 106 (8), pp. 929-934, Oct. 1, 2000.

EPO Office Action cited in 05751992.8, *EPO Office Action*, pp. 1-6, Nov. 2, 2010.

Office Action for U.S. Appl. No. 12/336,746, *U.S. PTO Office Action*, pp. 1-6, Nov. 9, 2010.

Yang et al., Deoxyxylothymidine 3'-O-Phosphorothioates: Synthesis, Stereochemistry and Stereocontrolled Incorporation into Oligothymidylates, *J. Bioorganic & Med. Chem. Lett.*, vol. 7, pp. 2651-2656, Jan. 1, 1997.

JP Office Action cited in JP App. No. JP2006-549430, *Japanese Office Action*, pp. 1-3, Jan. 4, 2011.

Office Action for U.S. Appl. No. 12/336,746, *U.S. PTO Office Action*, pp. 1-6 Mar. 28, 2011.

United States Patent and Trademark Office, "Non-Final Office Action," from related U.S. Appl. No. 12/336,746, dated Dec. 22, 2011, 8 pages.

\* cited by examiner

CHEMICALLY PROGRAMMABLE IMMUNITY

CROSS-REFERENCE TO RELATED APPLICATIONS

This application is a continuation of U.S. application Ser. No. 10/754,456 filed Jan. 9, 2004, now U.S. Pat. No. 7,645,743 which is a continuation-in-part of U.S. application Ser. No. 10/696,770 Oct. 29, 2003, now U.S. Pat. No. 7,422,746 which is a continuation-in-part of U.S. application Ser. No. 10/178,046 filed Jun. 21, 2002, now abandoned which is a continuation of PCT/US00/35179 filed Dec. 21, 2000, which claims the priority benefit of U.S. Application Ser. No. 60/171,707 filed Dec. 22, 1999.

FIELD OF THE INVENTION

The present invention relates to compositions and methods for providing immediate immunity to any desired antigen. "Immunity" is used herein to signify functional binding of immune components to a specific target. The specific target is not the same as, or structurally related to, the agent which generated the immunity in the first place, and in fact, by the methods disclosed herein, the nature of the target is determined not by an immunogen alone, but also by a pharmaceutical entity termed the "linker." The "linker" connects an immune response, elicited by one entity, the universal immunogen, to another entity, the target, by means of two structural recognition sites on the linker. The first of these sites binds to the recognition components of the immune response. The second of these sites binds to the target. Accordingly, the term "immunity" is used in a way so as to include a process not previously known in immunology referred to here as the altermune method. The immunity conferred by the altermune method is dependent on classical immunity, and can be seen as an extension or diversion of it.

BACKGROUND OF THE INVENTION

Immunization has been used for over a hundred years to protect humans and animals against disease. The premise of traditional immunization is that the most effective immune responses to an antigen, or a pathogen containing the antigen, occur after an individual is challenged with that same antigen two or more times. This phenomena is called immunological memory or a secondary immune response. When the immunization is successful, the individual is protected from the effects of the pathogen from which the antigen was derived.

For example, once an individual is successfully immunized with an antigen derived from a bacterial organism, the immune system in that individual is primed and ready to respond to that bacteria when it is encountered. Successful immunization requires that the antigen is located on an area of the bacteria that is accessible to the individual's immune system. When successful, the immune system responds, the bacteria is killed, contained, neutralized, or otherwise cleared from the body, and little or no disease results from the infection by the bacterial organism. The key to this protection is that immunization with the antigen must occur prior to the exposure to the bacterial organism from which the antigen is derived.

Accordingly, the traditional immunization process generally includes injecting an antigen into an individual, waiting an appropriate amount of time, and allowing the individual to mount an immune response. The time required for mounting an immune response is between approximately two weeks and several months for most antigens. In most cases, a booster administration of the antigen is required to maintain the immune response. This booster is normally given weeks or months after the initial administration of the antigen.

Therefore, traditional immunization is highly successful at providing protection if given several months in advance of exposure to an antigen, or pathogen, but traditional immunization is of little use when an individual is exposed to a new antigen to which the individual has not been previously exposed and an immediate effective immune response is required. A good example of such a situation is military troops in need of protection from bioterrorism agents. While a population of individuals can be vaccinated against agents of bioterrorism in advance of any potential exposure to the agents, traditional vaccination is not a simple answer. Traditional vaccination of a population creates harmful reactions in some persons and there is potential that the population may never be exposed to the agent, yet risks were taken. Additionally, a government cannot logistically develop, produce and vaccinate essential personnel with vaccines for every possible agent of bioterrorism. Accordingly, what is needed is a composition that can be administered either immediately before, or even after, an individual's contact, or suspected contact, with a pathogen, which administration allows for the generation of an immediate protective or effective immune response in the individual.

As alluded to above, another shortcoming of traditional immunization procedures is the requirement that the infectious pathogen, or a portion of the infectious pathogen, be administered to an individual. There are numerous incidences wherein vaccinations have themselves caused illness and even death because they contain a pathogen or a portion of a pathogen. Accordingly, what is needed is a composition that can be administered to an individual for immunization that does not contain a portion of the pathogen against which the individual is being immunized.

Still another shortcoming of traditional immunization procedures is the requirement that separate immunization procedures be used for each antigen, although in some cases several antigens are included in a single procedure. These separate immunization procedures are required because the natural memory, or secondary, immune responses are specific for the antigen to which the primary immune response was directed. Accordingly, what is needed is a "universal immunogen" that can be administered to an individual that will prime the individual's immune system for an immune response and a means to direct this immune response to new targets as the need arises. Alternatively, there is a need for the means to re-direct an existing immune response to a new target. Such a "universal immunogen," or the means of re-directing an existing immune response, would reduce the number of immunizations currently recommended for individuals.

SUMMARY OF THE INVENTION

The present invention provides compositions and methods for a programmable immunity that can provide a substantially immediate immune response by an individual against a target, such as a pathogen or other undesired substance. Since an immediate effective immune response is achieved, these compositions may be administered to an individual any time prior to the individual's contact with a pathogen or even soon after the individual's contact with a pathogen. In one embodiment, the present invention solves many of the problems facing the military regarding protection of their personnel from agents of bioterrorism.

The compositions and methods of the present invention also provide an advantage over traditional immunization techniques because the methods do not require that a modified pathogen or a portion of a pathogen be administered to an individual for effective immunization against that pathogen. Accordingly, the present invention will save the lives of people that currently have fatal adverse reactions to traditional vaccines.

The compositions of the present invention, in one embodiment, include an immunity linker, containing at least one first binding site that binds to an immune response component; and containing at least one second binding site that binds to a target. These linker compositions make use of a pre-existing immune response in an individual and link that pre-existing immune response to a different target, which is unrelated to the pre-existing immune response except for the connection between the two provided by the immunity linker. The pre-existing immune response is directed to an antigen containing the first binding site of the immunity linker and can be induced in the individual by administration of a universal immunogen containing the first binding site. Linking the immune response to the target allows for an immediate, linked immune response without the requirement for a primary immune response against the target.

The immunity linker can be any type of chemical or biological material including a microbe, a bacteriophage, a protein, a nucleic acid, a polysaccharide, a synthetic material or a combination thereof. In one embodiment, the at least one first binding site is physically or chemically linked or conjugated to a molecule comprising the at least one second binding site. In this embodiment, a spacer molecule may reside between the first binding site and the second binding site. In another embodiment, the immunity linker is a single molecule containing the at least one first binding site and the at least one second binding site.

A universal immunogen is administered to an individual and corresponds to, or contains, the first binding site of the immunity linker. Such administration causes the individual to mount a cellular and/or a humoral immune response, depending on the immunogen and the route of administration. If necessary, the universal immunogen can be administered with an adjuvant or other immune response enhancing materials. Additionally one or more booster administrations of the universal immunogen may be given to the individual at appropriate times. These methods of immunizing an individual are well known to one of ordinary skill in the art. The pre-existing immune response, alternatively, can be an immune response that does not require administration of a universal immunogen such as, but not limited to, the alpha-Gal response universal in humans as described herein.

Following the initiation or generation of a pre-existing immune response, if the individual is exposed, or is suspected of being exposed, to a novel compound or pathogen for which immediate immunity is desired, the individual is administered an immunity linker described herein that contains a first binding site that corresponds to the universal immunogen and a second binding site that binds to the novel compound or pathogen. The immunity linker binds at the one first binding site to the immune response components produced during the pre-existing immune response, and also binds to the novel compound or pathogen at the at least one second binding site thereby providing an immune complex of the immune response component bound to the immunity linker which is also bound to the novel compound or pathogen. The immune system of the individual recognizes these immunity linker complexes and removes or clears them from the body.

Thus, by administering a composition comprising an immunity linker described herein, the pre-existing immune response of the individual is re-directed from the universal immunogen to the novel compound or pathogen. As mentioned above, another benefit of the present invention is that only one initial immunizing molecule or universal immunogen is required for priming an individual's immune system for a later antigen-specific immune response. Thus, the present invention may decrease the number (and possibly the complexity of formulation) of vaccinations currently recommended or required for individuals. A further benefit of the present invention is the ease of preparation of the immunity linker and the universal immunogen. The immunity linkers of the present invention can be easily assembled and provided to health care professionals for rapid response to such public health needs as pandemic infections, bioterroristic threats, or limited outbreaks of specific pathogens. A still further benefit of the present invention is the breadth of compounds against which an individual can be immunized. Immunity linkers can be created that bind to any compound or foreign material such as antigens, pathogens, chemicals, or endogenous materials such as altered cells found in viral infections or cancer.

As previously mentioned, it is to be understood that the present invention can utilize an existing immune response in an individual. Thus, if an individual is already immune to a particular antigen, an immunity linker molecule can be made that has a first binding site comprising or corresponding to the antigen to which the individual is immune and the second binding site can be directed to the undesired pathogen, chemical or agent.

It should also be understood that the present invention allows for immune tuning, or in other words, allows for the selection of the type of immune response generated by the universal immunogen and/or the immunity linker, and thus allows for the selection of the type of immune response directed toward any particular target. Accordingly, a first binding site of a universal immunogen and/or an immunity linker may be chosen based upon whether the first binding site elicits a humoral immune response, a cellular immune response and/or an innate immune response.

These and other objects, features and advantages of the present invention will become apparent after a review of the following detailed description of the disclosed embodiments.

DETAILED DESCRIPTION OF THE INVENTION

The present invention is related to methods and compositions for immediately immunizing a human or animal against any molecule or organism, referred to herein as a target. This is referred to as chemically programmable immunity or programmable immunity. Programmable immunity differs from classical immunity in that programmable immunity allows for the re-direction of a pre-existing immune response directed toward one antigen, to the target. The immune response is re-directed using an immunity linker of the present invention.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth.

Immunity linkers of the present invention comprise at least two sites; (1) a first binding site that binds to at least one immune response component of an individual, and (2) a second binding site that binds to a target. The immune response component is one that exists in the individual prior to administration of the immunity linker to the individual. For example, the immune response component can be an antibody that was part of a previous immune response to the first binding site, or to a molecule, or a large assembly of molecules, or even a micro-organism containing the first binding site. Accordingly, as used herein, the term "pre-existing immune response" refers to an immune response that is directed toward the first binding site or an epitope that is immunologically similar to the first binding site. In other words, a "pre-existing immune response" is an immune response in which immune response components are generated or exist that bind to the first binding site. The pre-existing immune response can be generated by a previous administration to the individual of a universal immunogen that corresponds to a first binding site or can exist in the individual without such administration.

Accordingly, the present invention includes a method of diverting a pre-existing immune response in an individual from a first antigen to a target comprising, administering to the individual an effective amount of a composition comprising one or more immunity linkers, wherein the linkers comprise at least one first binding site and at least one second binding site, wherein the second binding site binds to the target and wherein the first antigen comprises the first binding site or an immunological equivalent thereof. The present invention also encompasses a method of increasing an immune response to a target comprising, administering to the individual an effective amount of a composition comprising one or more immunity linkers, wherein the linkers comprise at least one first binding site and at least one second binding site, wherein the second binding site binds to the target and wherein the individual has a pre-existing immune response to the first binding site or an immunological equivalent thereof.

Universal Immunogens

A universal immunogen that "corresponds to" a first binding site can be identical to the first binding site, can contain the entire first binding site, can contain a portion of the first binding site, or can be an immunological equivalent of the first binding site. When referring to two or more molecules, the term "immunological equivalent" refers herein to molecules that are bound by the same immune response component. The present invention only requires that the immune response component raised by the universal immunogen also bind to the first binding site. In one embodiment, the universal immunogen binds to the immune response component with sufficient affinity to result in the production of a complex that is capable of initiating or participating in an immune response. In a preferred embodiment, the cross-reactivity of the immune response component to molecules other than the universal immunogen and the first binding site is minimal.

The universal immunogen can be any molecule, organism or compound to which an individual mounts an immune response and can be administered via any route. The universal immunogen can be, but is not limited to, a molecule, a microbe, or a toxin or a toxoid derived therefrom; a protein or polypeptide; a polynucleotide; a polysaccharide; a synthetic material or a combination thereof. Preferably the universal immunogen causes an immune response in an individual that provides for long-lasting immune memory, can be re-administered to individuals in booster doses, and does not cause disease, pathology or long-term illness in individuals. An immunogen that comprises a portion of a pathogen or a modified portion of a pathogen can be a universal immunogen, but a universal immunogen is not required to bear any relationship to anything except the complementary immune response which it elicits. For example, humans are routinely immunized with immunogenic antigens from mumps virus, measles virus, tetanus toxoid, and poliovirus. Animals, such as cats and dogs, are routinely immunized with immunogenic antigens from rabies virus. These and other traditional immunogens can be used as universal immunogens, however, this would be a matter of convenience, not necessity.

Alternatively, non-traditional immunogens may be used as the universal immunogen. Preferably, a non-traditional immunogen does not contain either a portion or a modified portion of a pathogen. In one embodiment, the universal immunogen is a protein, or a portion of a protein, to which a hapten is bound. A "hapten" is defined herein as a molecule that reacts with a specific antibody but cannot induce the formation or generation of additional antibodies unless bound to a carrier protein or other large antigenic molecule. Most haptens are small molecules, but some macromolecules can also function as haptens. In one embodiment, performed for demonstration purposes and described herein as Example 1, the hapten is a phenylarsonate and the universal immunogen is a phenylarsonylated protein.

In another embodiment, the universal immunogen comprises a bacteriophage or an epitope of a bacteriophage. An immune response component can bind to any part of the bacteriophage and in one embodiment, binds to a peptide that is expressed on the surface of the bacteriophage. A bacteriophage universal immunogen can be administered to an individual via any route and in some embodiments, the bacteriophage can be contained within a bacteria as a convenient means of administration.

First and Second Binding Sites and Spacers of an Immunity Linker

The present invention is able to re-direct a pre-existing immune response directed toward a universal immunogen to a different antigen, in part, because the universal immunogen corresponds to a first binding site of an immunity linker. Since the first binding site is a part of both the universal immunogen and the immunity linker molecule, the pre-existing immune response, or the pre-existing immune system components, that are directed to the universal immunogen also recognize the immunity linker. The first binding site of the immunity linker can comprise a polypeptide, a polynucleotide, a polysaccharide, an organic chemical, a microorganism such as a bacteriophage, a bacterium, a virus or viral particle, or a protozoa, any fragment or portion of the foregoing, any combination of the foregoing, or any other composition that is recognized by the immune system of an individual or bound by an immune response component in an individual.

In one embodiment, the first binding site is the alpha-Gal epitope, i.e., galactosyl-alpha-1,3-galactosyl-beta-1,4-N-acetylglucosamine. In another embodiment, the first binding site comprises a portion of a bacteriophage, and more preferably, a polypeptide that is expressed on the surface of a bacteriophage.

The second binding site can comprise a polypeptide, a polynucleotide, a polysaccharide, an organic chemical, a microorganism such as a bacteriophage, a bacterium, a virus, a protozoa, or any fragment or portion of the foregoing, any combination of the foregoing, or any other composition that binds to a target. In one particular embodiment the first binding site and the second binding site are contained on the same microorganism. As used herein, polynucleotide or nucleic acid means either DNA or RNA, in any stranded conformation, e.g., single, double, triple, and any chemical modifications thereof, and contemplates the presence or absence of proteins associated with the nucleic acid. Chemical modifications can be in individual nucleotides prior to amplification or synthesis of the nucleic acids, or can be added to nucleotides after incorporation into multimers. Such modifications include, but are not limited to, modifications at cytosine, exocyclic amines, substitution of 5-bromo-uracil, backbone modifications, methylations, unusual base-pairing combinations and others known to those skilled in the art. In one embodiment, the second binding site comprises an antibody or an antibody fragment, preferably an antibody fragment containing an antibody variable region, and more preferably a Fab fragment. In another embodiment, the second binding site comprises a polypeptide expressed by a bacteriophage, and more preferably, a polypeptide that is expressed on the surface of a bacteriophage.

As described above, the immunity linker comprises any type of molecule or organism that contains a first binding site capable of binding to an immune response component, and contains a second binding site capable of binding a target. It is to be understood that the immunity linkers can contain more than one first binding site and/or more than one second binding site. The multiple first binding sites can be identical or can be different. The multiple second binding sites can also be identical or different. Binding sites may differ in their specificity for different molecules or their affinity for the same molecule. The immunity linker can also be modified to reduce its own immunogenicity.

Binding by the first and second binding sites to the immune response component and target, respectively, can be accomplished through any interaction including through binding provided by other molecules, such as polysaccharides or nucleic acids. In a preferred embodiment, a first binding site is specific for an immune response molecule and a second binding site is specific for a target. As described above, a molecule is "specific for" another molecule when the two molecules bind with sufficient affinity to result in the production of a functional complex for purposes of the immune system. In a further preferred embodiment, the cross-reactivity of one second binding site with molecules other than a target is minimal. In another preferred embodiment, the cross-reactivity of one first binding site with molecules other than an immune response component is minimal.

Following administration of the immunity linker to the individual, an immunity linker complex comprising the immune response component, the immunity linker, and the target is formed. The immunity linker can bind the target prior or subsequent to the binding of the immunity linker to an immune system component. Following formation of the immunity linker complex, the target is cleared via immune system pathways. A "clearing" of an antigen refers herein to the removal, inactivation or modification of the antigen such that it is no longer harmful to the body.

In another embodiment, the immunity linker comprises a first binding site that corresponds to an alpha-galactosyl, or alpha-Gal, epitope as is described in Galili, U. and Avila, J. L., Alpha-Gal and Anti-Gal, Subcellular Biochemistry, Vol. 32, 1999. Xenotransplantation studies have determined that humans mount an immune response to the alpha-galactosyl epitope, which is not normally found in humans, but is found in other animals and many microorganisms. In one particular embodiment of the present invention, the alpha-galactosyl epitope is conjugated to a second binding site that comprises an Fab fragment of an antibody.

In yet another embodiment, the immunity linker comprises a bacteriophage. The first binding site can correspond to any portion of the bacteriophage, but preferably corresponds to a first polypeptide expressed by the bacteriophage. A second binding site on the bacteriophage corresponds to a second and different bacteriophage-expressed polypeptide that binds to a target. Both the first and second polypeptides are expressed on the surface of the bacteriophage.

Example 3 below provides one example of a bacteriophage immunity linker as can be used in conjunction with a bacteriophage universal immunogen. In some embodiments, the immunity linker comprises a recombinant bacteriophage derived from a wild type bacteriophage by the method of phage panning. The first binding site consists of whatever portion (s) of the wild type bacteriophage function(s) immunogenically on the initial exposure of the subject to the wild type bacteriophage and is (are) still retained by the recombinant bacteriophage, which is used as a linker. The second binding site on the recombinant bacteriophage, used as a linker corresponds to a recombinant bacteriophage-expressed peptide that is selected because it binds to a target.

In another embodiment the immunity linker is a conjugate of the alpha-Gal epitope, acting as a first binding site, and a synthetic peptide, acting as a second binding site, the sequence of which peptide is derived from a bacteriophage panning experiment, wherein the peptide is panned from a random peptide library, displayed on a collection of recombinant bacteriophage, by the intended antigen attached to a solid support.

In other embodiments, the first and/or second binding sites comprise an aptamer nucleic acid, and more preferably an aptamer that has been produced by the SELEX process. SELEX stands for Systemic Evolution of Ligands by EXponential enrichment. SELEX methods are known in the art and are described in at least the following issued U.S. Pat. Nos. 5,475,096; 6,261,774; 6,395,888; 6,387,635; 6,387,620; 6,376,474; 6,346,611; 6,344,321; 6,344,318; 6,331,398; 6,331,394; 6,329,145; 6,300,074; 6,280,943; 6,280,943; 6,280,932; 6,261,783; and 6,232,071.

In general, the SELEX method relates to identifying nucleic acids that specifically bind to three dimensional targets. Nucleic acids have sufficient capacity for forming a variety of two- and three-dimensional structures and sufficient chemical versatility available within their monomers such that some sequences can be found that bind specifically with virtually any chemical compound. For purposes of stability in biological fluids, a preferred aptamer contains one or more modified nucleotides such as 2'-fluoro- or 2'-amino-2'-deoxypyrimidines. Nucleic acids using these bases are much more stable in vivo than naturally occurring nucleic acids. See, M. Famulok and G. Mayer, Cur. Top. Micro. Immunobiol. 243:123-146, 1999. Spiegelmers (see Vater, A. and Klussmann, S. Current Opin. Drug Discov. Devel. 2003 March; 6 (2):253-61) derived by similar methods may also be employed for their inherent stability in serum.

The first and second binding sites of the immunity linker described herein may be linked, or conjugated, by any means known to one of skill in the art. The terms “conjugated” and “conjugation” are defined herein to refer to a covalent or other form of linking two or more molecules. Conjugation can be accomplished by any means including, but not limited to, chemical means, genetic engineering means, or in vivo by biologic means. The first and second binding sites may be linked by a double stranded nucleic acid, a polypeptide, a chemical structure, or any other appropriate structure, or may be linked by a simple chemical bond.

In one particular embodiment the first and second binding sites of a linker are evolved in vitro in such as way that the first binding site will only interact with the immune response component after the second binding site has bound to the target. Allosteric interactions leading to such behavior are well-known in proteins and other macromolecules, and could be a component of the selection process in the in vitro evolution of the linker. The linker may also be made by nanofabrication methods.

Immune Response Components As stated above, the one or more first binding sites of the immunity linker bind to an immune response component. The term "immune response component" is used herein to refer to any molecule or cell involved in an immune response of an individual. The term "individual" encompasses both animals and humans. Non-limiting examples of immune response components are antibodies; lymphocytes including, but not limited to, T cells, B cells and natural killer cells; macrophages; granulocytes including, but not limited to, neutrophils, basophils and eosinophils; and receptors on any of the foregoing cells including, but not limited to, T cell receptors and B cell receptors. A humoral immune response component includes an antibody. The term antibody includes all of the classes and subclasses of antibodies, IgG, IgM, IgA, IgD, IgE, etc., secretory and excreted forms of the antibodies, fragments of antibodies, including variable, hypervariable and constant regions, heavy and light chains, combinations of fragments and mixtures of fragments and whole antibodies. Such antibodies can be humanized, polyclonal or monoclonal, naturally derived or synthetic antibodies.

In one embodiment, at least one first binding site binds to the active binding site of the immune response component. For example, if the immune response component is an antibody such as an IgG molecule, the first binding site of the immunity linker is the antigenic epitope to which the active binding site of the variable region of the IgG molecule normally binds.

Targets

The one or more second binding sites of the immunity linkers bind to a target, and preferably the second binding site is specific for the target. The term "target" refers herein to any composition to which an increased immune response is desired in an individual.

In one embodiment, the antigen is a compound or organism to which the subject individual has not been exposed. However, the antigen may also be a compound or organism, to which the subject individual has been exposed but to which an optimal immune response has not been mounted.

Targets include, but are not limited to, antigens, microorganisms, pathogens, viruses, viral particles, bacteria, polypeptides, toxic chemicals, non-self molecules, and any fragments, portions or combinations thereof. As used herein, targets also include molecules or compositions that are not normally targeted by an immune response in an individual, such as molecules identifiable as self, molecules too small to be responded to by the immune system, nonimmunogenic compounds or chemicals, and molecules or materials that are sequestered from the immunogenic components of the immune system. In one embodiment, the target is an antibody or cellular component of the immune system that the individual wants to eliminate so as to relieve an autoimmune disorder.

Immunity Linker Populations

As indicated above, the immunity linkers of the present invention can have more than one first binding site and/or more than one second binding site. The present invention also encompasses the use of one or more populations of immunity linkers wherein each population has a different first binding site and/or second binding site. The multiple binding sites may differ either in their specificity for different molecules or epitopes or their affinity for the same molecule or epitope. In one embodiment of the present invention, the immunity linker comprises two or more second binding sites, each specific for a different target. In another embodiment, the immunity linker comprises two or more second binding sites, each specific for different epitopes on the same target. In yet another embodiment, the immunity linker comprises two or more second binding sites, each specific for the same epitope on a target but having different affinities for the target.

In still other or further embodiments, the immunity linker comprises two or more first binding sites, each capable of binding to a different immune response component. In yet another embodiment, the immunity linker comprises two or more first binding sites, each capable of binding to different sub-structures of the same immune response component. In another embodiment, the immunity linker comprises two or more first binding sites, each capable of binding to the same sub-structure of an immune response component but having different affinities for the immune response component.

The immunity linkers of the present invention can have any combination of the aforementioned multiple first binding sites and second binding sites. The present invention also encompasses the administration of different populations of immunity linkers, each population having any combination of the aforementioned multiple first binding sites and second binding sites.

In one embodiment, a population of immunity linkers is administered to an individual, wherein each linker has an identical first binding site and the second binding sites are all aptamers, that bind to the same target, but with different affinities for the target. In another embodiment, a population of immunity linkers is administered to an individual, wherein each linker has an identical first binding site and the second binding sites are all antibodies, or portions of antibodies, that bind to different targets. In still other embodiments, the immunity linkers of the population all have an identical first binding site and different types of second binding sites, i.e., antibody binding sites, aptamer binding sites, etc., where each second binding site is specific for the same target or different targets.

The present invention contemplates populations of immunity linkers that comprise at least one first binding site described herein. Such populations can have immunity linkers all having first binding sites having the same binding specificity or combinations of binding specificities. Further, the binding may be accomplished by first binding sites of the same type, such as all being nucleic acid molecules or all proteins, which may have the same or different binding specificities. The binding may be accomplished by first binding sites of different types on one immunity linker or a population of different immunity linkers with differing first binding sites. The first binding sites of different types can have the same or different binding specificities for one or more immune response components.

Additionally, the present invention contemplates populations of immunity linkers that comprise at least one second binding site described herein. Such compositions comprise immunity linkers all having second binding sites having the same binding specificity or combinations of binding specificities. Further, the binding may be accomplished by second binding sites of the same type, such as all being nucleic acid molecules or all proteins, which may have the same or different binding specificities. The binding may be accomplished by second binding sites of different types on one immunity linker or a population of different immunity linkers with differing second binding sites. The second binding sites of different types can have the same or different binding specificities for one or more targets.

Thus, the compositions comprise immunity linkers in which the binding specificity of the at least one first binding site and the binding specificity of the at least one second binding sites are all uniform, that is, each first binding site has the same binding specificity for its binding partner and each second binding site has the same binding specificity for its binding partner. Alternatively the compositions may comprise multiple immunity linker populations each population having first binding sites with differing binding specificities and also having second binding sites with differing binding specificities.

Methods of Use

The present invention comprises methods and compositions for diverting a pre-existing immune response in an individual from a first target to a second target. In some embodiments, both the first target and the second target are different antigens. Since the first antigen, or an immunological equivalent of the first antigen, is present in the linker molecule, the "diverting" of an immune response does not require a cessation of the immune response to the first antigen. The present invention further provides methods and compositions for increasing an immune response to a target in an individual. A previous immune response to the target may or may not already exist in the individual. The present invention also provides chemically programmable immunity for individuals that provide for the immediate and specific immunization of the individual against a pathogen or other undesired substance.

According to the present invention, the individual is first immunized with a universal immunogen. The individual can then be immediately immunized against a chosen target simply by administering to the individual a composition comprising an immunity linker with at least one first binding site that binds to an immune response component and a second binding site that binds to a target. Any combination of universal immunogen and immunity linker described herein can be used with the only requirement that the first binding site of the immunity linker will be bound by some of the immune response components produced as a result of inoculation by the universal immunogen. Immunity to the universal immunogen may occur as a result of an intentional inoculation or, as in the case of the alpha-Gal epitope and its attendant anti-Gal immunity, by natural processes.

The present invention may be particularly useful in the military where troops may be unexpectedly exposed to a pathogen, toxin, or to a toxic chemical substance. Military personnel are pre-immunized with a universal immunogen that corresponds to the first binding site of an immunity linker. If the military personnel are unexpectedly challenged or believed to be challenged with a pathogen, toxin, or chemical agent, the immunity linker, having a second binding site that binds the pathogen, toxin, or chemical agent, is administered to the military personnel, thereby immediately protecting them against the pathogen.

The present invention can be used to prevent and/or treat disease or infection from organisms including, but not limited to, anthrax, dengue virus, and Marburg virus. For example, upon detecting anthrax in a combat zone, immunity linkers specific for anthrax are administered orally to the troops and civilians previously immunized with the universal immunogen and protection against anthrax is conferred. The immunity lasts as long as the personnel continue to maintain adequate in vivo concentrations of immunity linkers. In one embodiment, immunity linkers are administered to the individuals on a continuing basis in order to maintain adequate in vivo concentrations of immunity linkers. Immunity linkers can be administered at any interval including, but not limited to, hourly, daily, weekly, or monthly intervals. In the case of immunity linkers that must necessarily be administered for a long period of time, linkers are sought wherein the second binding site is not itself immunogenic. Once the threat is passed, administration of immunity linkers is stopped. Possible side effects of the present invention are therefore temporary, unlike traditional immunizations which often generate long-lasting side effects or complications in immunized humans or animals.

With regard to the more general population, pharmacies can have a library of different immunity linkers available for a variety of different pathogens and toxic substances. Once an individual is pre-immunized with a universal immunogen, administration of one or more of these different immunity linkers results in the generation of a protective immune response against the variety of different pathogens and toxic substances.

One example of an infection treatable by the present invention is the flu or infection by an influenza virus. By using the immunity linkers of the present invention, there is no need to develop a new strain of vaccine every year to respond to the new strain of influenza of that year. Only one portion of the immunity linker needs to be altered as the influenza virus alters its antigenic markers. The at least one second binding site can be changed each year, or as needed, to that which binds to the new influenza virus of that occurrence. Preferably, the at least one second binding site is a DNA aptamer made from modified nucleotides. Such DNA molecules are very stable against metabolic enzymes. For example, individuals can inhale compositions of immunity linkers having the appropriate first and second binding sites to prevent the attachment and infection by influenza virus. This inhalation therapy continues as long as necessary and is stopped when the influenza season has passed.

It should be understood that the present invention also allows for immune tuning, or in other words, allows for the selection of the type of immune response generated by the universal immunogen and/or the immunity linker, and thus allows for the selection of the type of immune response directed toward any particular target. A first binding site of a universal immunogen and/or an immunity linker may be chosen based upon whether the first binding site elicits a humoral immune response, a cellular immune response and/or an innate immune response. A humoral immune response is defined herein as an immune response mediated predominantly by antibodies. A cellular immune response includes an immune response mediated predominantly by T cells. A first binding site may also be chosen based upon whether it elicits a $CD4^+$ T cell response or a $CD8^+$ T cell response. As used herein, a $CD4^+$ T cell response is an immune response mediated predominantly by $CD4^+$ T cells as compared to $CD8^+$ T cells, whereas a $CD8^+$ T cell response refers herein to an immune response mediated predominantly by $CD8^+$ T cells as compared to $CD4^+$ T cells. An innate immune response includes an immune response mediated predominantly by macrophages and/or NK cells. Accordingly, the present invention includes immunity linkers and universal immunogens that contain a first binding site that elicits a humoral immune response, a cellular immune response, an innate immune response, a $CD4^+$ T cell immune response and/or $CD8^+$ T cell immune response.

The ability to tailor the immune response generated by the universal immunogen and/or the immunity linker is important. In some diseases, chlamydia infections of the eye, for instance, it is thought by some that the immune response is the cause of the pathology. Having control of the nature of the immune response independent of the nature of the pathogen may have an important role in treatment. For instance, it may be the cellular component of the immune response to chlamydia that leads to blindness; if so, the altermune therapy of the present invention for chlamydia could be based on an immunity, which does not invoke a cellular immune component, killing the bacteria through a T cell-independent mechanism.

Thus unlike the natural immune system, and for the first time, the profile of an immune response can be tailored by a physician using the present invention and not predetermined by the nature of the pathogen itself.

Accordingly, the present invention includes a method of increasing a humoral immune response, a cellular immune response, a CD4$^+$ T cell immune response, and/or a CD8$^+$ T cell immune response in an individual to which a universal immunogen and/or an immunity linker are administered. These immune responses may or may not be the type of immune response that would occur naturally in an individual in response to a particular target. In some embodiments, the immune response is different from that which would or does occur naturally in an individual in response to a particular target. In one embodiment, a universal immunogen and an immunity linker are administered to an individual that contain a first binding site that elicits a humoral immune response, wherein the second binding site of the immunity linker binds to a target that usually elicits a cellular immune response in that or other individuals.

The present invention further comprises methods for removing other unwanted materials from the body of a human or animal by administering a composition comprising an immunity linker. The immunity linkers can be used to remove excess or unwanted molecules or chemicals synthesized by the body or found in the body, including but not limited to, proteins, fats, nucleic acid polymers, hormones, cellular factors, neurochemicals, toxic cellular factors, apoptotic factors, cellular signal molecules, antibodies or unwanted cells, minerals such as calcium or magnesium and compounds comprising combinations or mixtures of these and other molecules. It is contemplated that in some cases, complex methods might be employed to remove unwanted cells such as marking them in such a way as to make them susceptible to immunity linker binding. The immunity linkers can be used to remove any unwanted material from the body by providing a second binding site that binds the unwanted material and using the first binding site's binding to an immune response component such that the body's natural clearance mechanisms are enlisted to remove the unwanted material. Any material that can be bound by the second binding site can be effected or removed by the methods of the present invention, thus the list of materials that can be effected or removed is only limited by the ability to provide a binding partner for the unwanted material. Providing binding partners for unwanted materials is well within the scope of skilled practitioners and includes both the methods discussed herein and others used by those skilled in the art.

With the methods and compositions of chemically programmable immunity, an immune response can be used to clear or contain these unwanted materials such as if an immune response had been elicited by the unwanted material directly. For example, antibody complexes, comprising immunity linkers, bound at one site to antibodies and at another site to the unwanted material, are removed by the body's immune clearance mechanisms. Containment of the target can comprise mechanisms such as those wherein cells wall-off or form bathers around the immunity linker bound to the unwanted material, similar to the cellular response used to wall off tuberculosis pathogens. In some methods, artificial mechanisms such as plasmaphoresis methods, wherein the blood or other fluids are filtered outside of the body, can be used to entrap the immune complexes or cellular complexes formed with immunity linkers. Specific removal of bound immunity linkers can be used, for example by using columns or separation systems using antibodies to the immunity linker itself.

Accordingly, the present invention may be used for the treatment of multiple infections, diseases and conditions. The terms "treatment," "treating," "treat," and the like are used herein to refer generally to obtaining a desired pharmacological and/or physiological effect. The effect may be prophylactic in terms of completely or partially transferring immunity from one antigen to another and/or may be therapeutic in terms of a partial or complete stabilization or cure for a disease and/or adverse effect attributable to the disease. "Treatment" as used herein covers using the immune response directed to one antigen for the control of another antigen or its effects such as any treatment of a disease in a subject, particularly a human, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom. The terms "treatment," "treating," "treat," and the like also include the reduction, control or containment of an unwanted substance, including an antigen, in an individual. The amount of reduction of a substance may be determined by any method.

The expression "therapeutically effective amount" refers to an amount of, for example, a composition disclosed herein, that is effective for preventing, ameliorating, treating or delaying the onset of a disease or condition. A "prophylactically effective amount" refers to an amount of, for example, a composition disclosed herein that is effective for preventing a disease or condition.

Methods of Administration

According to the present invention, a universal immunogen is administered to an individual prior to administration of a corresponding immunity linker. A universal immunogen can be administered at any time prior to administration of a corresponding immunity linker and may be administered multiple times prior to administration of a corresponding immunity linker. These multiple administrations may be referred to as "booster" administrations. One method contemplated by the present invention comprises multiple administrations of different universal immunogens. With administrations of different universal immunogens, the repertoire of possible immune linkers is increased.

Multiple administrations of immunity linkers are also included in the present invention. Methods include immunization of an individual using one universal immunogen followed by one or more administrations of the same or different immunity linkers. Methods also include immunization of an individual using several different universal immunogens followed by one or more administrations of the same or different immunity linkers.

It is preferred that immunity linkers are administered to an individual for as long as is needed and at appropriate intervals to maintain adequate in vivo concentrations of the immunity linkers to treat an infection or disease or to remove sufficient amounts of an unwanted material from the individual. Immunity linkers can be administered at any interval including, but not limited to, hourly, daily, weekly, or monthly intervals, or any division thereof. Appropriate administration intervals can be determined by those of ordinary skill in the art and are based on the identity of the target or pathogen, the amount of target or pathogen detected in the individual, duration of exposure, immune linker pharmacokinetics, characteristics of the individual such as age, weight, gender, etc., and any other relevant factors. The time of administration of immunity linker will need to be empirically determined and could vary with particular pathogen, toxin, duration of exposure, linker pharmacokinetics, etc.

The universal immunogens and immunity linkers of the present invention are administered to individuals using any appropriate route. Appropriate routes of administration include, but are not limited to, oral, inhalation, parenteral, subcutaneous, intramuscular, intravenous, intrarticular, intrabronchial, intraoccular, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, subcutaneous, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, transmucosal, intranasal, iontophoretic means, and transdermal means. Differing types of immune response are sometimes triggered by different routes of administration of an antigen, and the preferred route for the particular immune response is known to those skilled in the art. The present invention is not limited by the route of administration of the universal immunogen or immunity linker.

With regard to the bacteriophage linker molecules and bacteriophage universal immunogens, both can be administered as the purified phage or as a bacterial clone containing it. In a preferred embodiment, a lytic bacteriophage is administered to an individual as a portion of, or contained within, a bacteria. The bacteriophage can be delivered by known administration methods that would allow for an optimum response to the target.

The compositions described herein are also contemplated to include pharmaceutical compositions comprising immunity linkers or universal immunogens and at least one of any suitable auxiliary such as, but not limited to, diluent, binder, stabilizer, buffers, salts, lipophilic solvents, preservative, adjuvant or the like. Pharmaceutically acceptable auxiliaries are preferred. Examples and methods of preparing such sterile solutions are well known in the art and can be found in well known texts such as, but not limited to, REMINGTON'S PHARMACEUTICAL SCIENCES (Gennaro, Ed., 18th Edition, Mack Publishing Co. (1990)). Pharmaceutically acceptable carriers can be routinely selected that are suitable for the mode of administration, solubility and/or stability of the compound. Pharmaceutical excipients and additives useful in the present invention include, but are not limited to, proteins, peptides, amino acids, lipids, and carbohydrates. The pharmaceutical compositions comprising the compounds of the present invention can also include a buffer or a pH adjusting agent. Additionally, pharmaceutical compositions of the invention can include polymeric excipients/additives.

The term "adjuvant" as used herein is any substance whose admixture with the universal immunogen increases or otherwise modifies the immune response generated thereby. Any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), Titermax® (polyoxyethylene-polyoxypropylene copolymer adjuvants from CytRx Corporation), modified lipid adjuvants from Chiron Corporation, saponin derivative adjuvants from Cambridge Biotech, killed *Bordatella pertussis*, the lipopolysaccharide (LPS) of gram-negative bacteria, large polymeric anions such as dextran sulfate, and inorganic gels such as alum, aluminum hydroxide, or aluminum phosphate.

For oral administration, pharmaceutical compositions can be in the form of a tablet or capsule, such as discrete units such as capsules, cachets or tablets each containing a predetermined amount of the immunity linkers; as a powder or granules; as a solution or a suspension in an aqueous liquid or a non-aqueous liquid; or as an oil-in-water liquid emulsion or a water-in-oil emulsion and as a bolus, etc. A tablet may be made by compression or molding, optionally with one or more accessory ingredients. The tablets may be optionally coated or scored and may be formulated so as to provide a slow or controlled release of the active ingredient therein. In one embodiment, the immunity linker or universal immunogen is provided by orally administering *E. coli* infected with a bacteriophage immunity linker or bacteriophage universal immunogen.

In addition, the compositions of the present invention may be incorporated into biodegradable polymers allowing for sustained release of the immunity linkers, for example, the polymers being implanted for slow release of the immunity linkers. Biodegradable polymers and their uses are described, for example, in detail in Brem et al., 74 J. NEUROSURG. 441-46 (1991).

Formulations suitable for parenteral administration include aqueous and non-aqueous sterile injection solutions which may contain anti-oxidants, buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the immunity linkers or universal immunogens to be administered in a suitable liquid carrier. The liquid forms may include suitably flavored suspending or dispersing agents such as the synthetic and natural gums, for example, tragacanth, acacia, methyl-cellulose and the like. Formulations for rectal administration may be presented as a suppository with a suitable base comprising, for example, cocoa butter or a salicylate. Formulations suitable for vaginal administration may be presented as pessaries, tamports, creams, gels, pastes, foams or spray formulations containing in addition to the active ingredient such carriers as are known in the art to be appropriate.

The compositions of the present invention may also be entrapped in microcapsules prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nanoparticles and nanocapsules) or in macroemulsions. REMINGTON'S PHARMACEUTICAL SCIENCES (A. Osol ed., 16th ed. (1980)).

The present invention provides stable formulations as well as preserved solutions and formulations containing a preservative as well as multi-use preserved formulations suitable for pharmaceutical or veterinary use, comprising the immunity linker compositions disclosed herein in a pharmaceutically acceptable formulation.

In general, the compositions disclosed herein may be used alone or in concert with therapeutic agents at appropriate dosages defined by routine testing in order to obtain optimal efficacy while minimizing any potential toxicity. The dosage regimen utilizing a composition of the present invention may be selected in accordance with a variety of factors including type, species, age, weight, sex, medical condition of the patient; the severity of the condition to be treated; the route of administration; the renal and hepatic function of the patient; and the particular composition or therapeutic agent employed. A physician or veterinarian of ordinary skill can readily determine and prescribe the effective amount of the immunity linker and/or universal immunogen required to prevent, counter, or arrest the progress of the condition.

The dosages of a composition disclosed herein may be adjusted when combined to achieve desired effects. Methods are known in the art for determining effective doses for therapeutic and prophylactic purposes for the disclosed pharmaceutical compositions. More specifically, the pharmaceutical compositions may be administered in a single dose, or a single daily dose or the total daily dosage may be administered in divided doses of two, three, or four times daily. The dosage of the compositions may be varied over a wide range from about 0.0001 to about 1,000 mg per individual or until an effective response is achieved. The range may more particularly be from about 0.001 mg/kg to 10 mg/kg of body weight, about 0.1-100 mg, about 1.0-50 mg or about 1.0-20 mg, for adults (at about 60 kg). The compositions may be administered on a regimen of about 1 to about 10 times per day, for one or multiple days, or once a week or once a month, or until an effective response is achieved. The pharmaceutical compositions of the present invention may be administered at least once a week over the course of several weeks or months. Data obtained from cell culture assays and animal studies may be used in formulating a range of dosages for use in humans.

In addition, co-administration or sequential administration of the compositions of the present invention and other therapeutic agents may be desirable. A composition described herein can be administered during, before or after administration of any other therapeutic agent.

Methods of Production

Immunity linkers can be made in many ways, several of which are described herein and are not to be seen as limiting the methods of making immunity linkers. The universal immunogen, or first binding site, can be physically linked or conjugated, such as with known chemical conjugation methods or molecules, to a molecule or organism with the at least one second binding site that binds the target. In another embodiment, the immunity linker can be produced or manufactured as a single molecule containing the first and second binding sites. The immunity linker may also comprise an organism. In yet another embodiment, the immunity linker consists of two active binding sites connected together by a rigid or flexible spacer such as a double helical region of RNA or DNA. A function of the spacer is to hold the two ends of the linker together, while preventing them from interacting.

The first and second binding sites of the present invention may be identified and isolated by any method. Methods for isolating binding moieties for a target or immune response component can be determined using methods such as those of Mario Geysen. Geysen, et al., PNAS 1984 81 (13):3998-4002 and Geysen et al., J. Immunol. Methods, 1987, 102 (2) 259-74 describe an early method of peptide synthesis and screening, using Geysen's pin apparatus. Improvements to the original method and applications of the methods have been taught in many publications, including, but not limited to, publications such as Geysen, et al., Chem. Biol. 1996, 3 (8):679-88; Schultz et al., Biotechnol. Prog., 1996, 12 (6):729-43; Carter, J M, Methods Mol. Biol. 1994, 36:207-23 (Geysen PEPSCAN procedure); Int. J. Pept. Protein Res. 1993, 42 (1):1-9; Wagner et al., Comb. Chem. High Throughput Screen 1998 1(3):143-153; Edmundson, et al., Proteins, 1993, 16 (3):246-67; Alexander et al., PNAS 1992 89 (8):3352-6; Edmundson, et al., Ciba Found. Sump 1991, 158:213-25; Rodda et al., Australas Biotechnol. 1993, 3 (6) 346-7; Tribbeck et al., J. Immunol. Methods 1991, 139 (2):155-66; Smith, G. P., Curr. Opin. Biotechnol. 1991, 668-73.

These combinatorial synthesis methods can be used to rapidly determine binding peptides that function as second binding sites in binding the target. Randomly generated peptides can also be rapidly tested for binding to the target and provide second binding sites for binding to the target. These peptides, protein fragments or peptides can be conjugated to the first binding site to form an immunity linker.

In several embodiments of the present invention, the universal immunogen comprises a first bacteriophage expressing a first polypeptide, and the immunity linker comprises a second bacteriophage expressing both the first polypeptide and a second polypeptide. In some embodiments, the first bacteriophage is a wild-type form of a bacteriophage and the second bacteriophage is a mutant, or recombinant, form of the same bacteriophage. Phage display techniques can be used to select for a bacteriophage expressing either or both the first polypeptide and the second polypeptide. More specifically, phage display is a selection technique in which a peptide or protein is expressed as a fusion with a coat protein of a bacteriophage, resulting in display of the fused protein on the exterior surface of the phage virion. Phage display allows for the selection of a peptide displayed on the outside of a bacteriophage that binds to a target. This peptide, or some part of it, functions as the second binding site.

Methods for making the nucleic acid aptamers, which form one embodiment of a first and/or second binding site are known in the art and are taught at least in several patents referenced above. In general, the methods comprise making a nucleic acid ligand for any desired target. The methods involve selection from a mixture of nucleic acid candidates and step-wise iteration of structural improvement using the same general selection theme, to achieve virtually any desired criterion of binding affinity and selectivity. For example, the SELEX method allows for isolation of a single sequence variant in a mixture containing at least $10^{14}$ sequence variants. Aptamers generated using the SELEX methods or improvements or other methods are then used as the second binding sites for immunity linkers. The aptamers to any target can be generated in hours or days, linked to the linker portion and the first binding site of the immunity linker, and provided for protection of a population.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It should be understood, of course, that the foregoing relates only to preferred embodiments of the present inven-

Example 1

Administration of *Haemophilus influenzae* Type B Immunity Linker to Neonatal Rats

*Haemophilus influenzae* Type B (Hib) is an encapsulated bacterial pathogen that causes serious invasive diseases, particularly in young children and the immunocompromised. The protective immune response to Hib is directed against epitopes of the capsular polysaccharide (PS). It is known that passive administration of anti-capsular polysaccharide antibody to rats inoculated with 10-100 Hib organisms intraperitoneally prior to infection will protect them against bacteremia/sepsis. The primary effector mode of protection against Hib is by the complement-dependent bactericidal activity of the anti-PS antibodies.

For purposes of the present invention, a human Fab fragment specific for the Hib capsular polysaccharide (PS) was cloned. While this Fab fragment uses the same heavy and light chain variable regions of "native" antibodies, it lacks the CH2 and CH3 domains of the IgG heavy chain. Accordingly, this Fab fragment alone is unable to bind complement and manifest bactericidal/protective activity. The Fab fragment (Fab41) serves as the second binding site of the immunity linker. This Fab fragment was linked to a phenylarsonate hapten that serves as the first binding site of the immunity linker. The resulting immunity linker was labeled Fab41-ARS.

Neonatal rats received a subcutaneous injection of anti-phenylarsonate antibodies made by injecting phenylarsonated keyhole limpet protein into adult rats and affinity purifying the antibodies produced on a phenylarsonate column. Eighteen hours later, Hib organisms were administered intraperitoneally to the neonatal rats. Two hours later, Fab41-ARS, the linker, was injected intraperitoneally into the neonatal rats. Eighteen to twenty-four hours later, blood from the neonatal rats was plated on chocolate agar and Hib colonies counted. The results are shown in Table 1 below.

TABLE 1

| Group | Anti-ARS | Fab41-ARS | Hib CFU/ml |
|---|---|---|---|
| 1 | — | — | $>10^6, >10^6, >10^6$ |
| 2 | +(1.0 mg) | — | $>10^6, 10^5, 4 \times 10^4$ |
| 3 | +(0.1 mg) | — | $>10^6, 1.3 \times 10^5, 5.5 \times 10^4$ |
| 4 | — | +(100 µg) | $>10^6, >10^6, >10^6$ |
| 5 | — | +(10 µg) | $>10^6, >10^6, >10^6$ |
| 6 | — | +(1.0 µg) | $>10^6, >10^6, >10^6$ |
| 7 | +(1.0 mg) | +(100 µg) | $2.2 \times 10^4, <20, <20$ |
| 8 | +(1.0 mg) | +(10 µg) | $4.5 \times 10^4, 1.1 \times 10^4, 4 \times 10^2$ |
| 9 | +(1.0 mg) | +(1.0 µg) | $4.5 \times 10^4, 4.4 \times 10^4, 1.3 \times 10^4$ |
| 10 | +(0.1 mg) | +(100 µg) | $<20, <20, <20$ |
| 11 | +(0.1 mg) | +(10 µg) | $1.0 \times 10^5, 2.1 \times 10^4$ |
| 12 | +(0.1 mg) | +(1.0 µg) | $1.1 \times 10^5, 7.2 \times 10^4, 6.6 \times 10^4$ |

Sterile PBS-BSA administered where indicated by (—).
Each cfu value represents results for an individual neonatal rat.

Example 2

Alpha-Galactosyl Epitope Immunity Linker

Recombinant knock-out mice lacking alpha-1,3-galactosyltransferase and consequently have a B- and T-cell immune response to its product, the alpha-1,3-galactosyl-galactose bond or alpha-galactosyl epitope, are administered an immunity linker containing an alpha-galactosyl epitope. The alpha-galactosyl epitope is described in Galili, U. and Avila, J. L., Alpha-Gal and Anti-Gal, Subcellular Biochemistry, Vol. 32, 1999. The immunity linker comprises Gal(alpha 1,3) Gal (beta 1,4)-GlcNAc-R, where the R represents a human Fab fragment specific for the capsular polysaccharide of *Haemophilus influenzae* type b (Hib). Ten minutes later, the mice are intraperitoneally administered a significant live dosage of Hib. After 24 hours, by plating their blood on chocolate agar, the number of cfu in the blood of the experimental mice is compared to the same measure in mice that have received the pathogen but not the prior treatment with the immunity linker. The treatment with the Fab fragment linked to the alpha-galactosyl epitope inhibits the bacteremia relative to mice which had not received the linker. At some amounts of linker, inhibition is dose dependent.

Example 3

Development of Phage Display Immunity Linkers with Specificity for Anthrax

1. Using standard phage display techniques, such as that sold by New England BioLabs, with random oligonucleotides coding for a large number of random peptides, isolate a recombinant bacteriophage that displays a peptide that is specific for *B. anthracis* spores, or other toxins, toxin components (such as PA) or antigens of *B. anthracis*.
2. Demonstrate in vitro that the recombinant bacteriophage acts as an immunity linker by 1) the binding of antibodies to a non-recombinant form of the bacteriophage and to the recombinant bacteriophage and 2) the binding of the recombinant bacteriophage to the anthrax spores.
3. Immunize a subject with the non-recombinant bacteriophage. This immunization occurs by injection or by inhalation.
4. Expose the subject to a composition comprising the recombinant bacteriophage that expresses the anthrax spore binding peptide. Using inhalation administrative routes, provide adequate amounts of the composition effective to prevent anthrax infection in the lungs of the subject.
5. Upon exposure of the subject to anthrax through inhalation means, the subject is protected from infection by inhalation-type anthrax.

Such procedures could also be used to stop or inhibit cutaneous or gastrointestinal anthrax exposure.

What is claimed is:

1. A method of increasing a humoral immune response to a target in an individual comprising,
   administering to the individual an effective amount of a composition comprising one or more immunity linkers,
   wherein the linkers comprise at least one first binding site and at least one second binding site,
   wherein the first binding site binds to any humoral immune response component of a pre-existing immune response,
   wherein the second binding site binds to the target, and
   wherein the target normally elicits a cellular immune response in the individual.

2. The method of claim 1, wherein the target is a cancer cell or viral infected cell.

3. The method of claim 1, wherein the target is a cancer cell.

4. The method of claim 1, wherein the at least once second binding site is an aptamer nucleic acid.

5. The method of claim 1, wherein the one or more immunity linkers comprise, two or more first binding sites that differ in a) specificity for different sub-structures on the immune response component, or b) affinity for the same sub-structures on the immune response component.

6. The method of claim 1, wherein the at least one second binding site comprises an antibody or a fragment thereof.

7. The method of claim 1, wherein the one or more immunity linkers comprise two or more second binding site that differ in a) specificity for different epitopes on the target, or b) affinity for the same epitope on the target.

8. A method of tuning or tailoring a humoral or innate immune response to a target in an individual comprising, administering to the individual an effective amount of a composition comprising one or more immunity linkers, wherein the linkers comprise at least one first binding site that binds to any humoral or innate immune response component of a pre-existing immune response, further comprising at least one second binding site that binds to the target, and wherein the target normally elicits a cellular immune response in the individual.

9. The method of claim 8, wherein the target is a pathogen.

10. The method of claim 8, wherein the target is an altered cell.

11. The method of claim 10, wherein the altered cell is a cancer or viral infected cell.

12. The method of claim 8, wherein the at least one second binding site comprises an aptamer nucleic acid.

13. The method of claim 8, wherein the at least one second binding site comprises an antibody or a fragment thereof.

14. The method of claim 8, wherein the one or more immunity linkers comprise two or more first binding site that differ in a) specificity for different sub-structures on the immune response component, or b) affinity for the same sub-structures on the immune response component.

15. The method of claim 14, wherein the immune response component comprises an antibody.

16. The method of claim 8, wherein the one or more immunity linkers comprise two or more second binding site that differ in a) specificity for different epitopes on the target, or b) affinity for the same epitope on the target.

* * * * *